United States Patent
Souriau et al.

(10) Patent No.: US 11,812,559 B2
(45) Date of Patent: Nov. 7, 2023

(54) FLEXIBLE ELECTRONIC STRUCTURE AND METHOD FOR PRODUCING SAME

(71) Applicant: COMMISSARIAT A L'ENERGIE ATOMIQUE ET AUX ENERGIES ALTERNATIVES, Paris (FR)

(72) Inventors: Jean-Charles Souriau, Grenoble (FR); Xavier Baillin, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 17/263,772

(22) PCT Filed: Jul. 29, 2019

(86) PCT No.: PCT/FR2019/051865
§ 371 (c)(1),
(2) Date: Jan. 27, 2021

(87) PCT Pub. No.: WO2020/025889
PCT Pub. Date: Feb. 6, 2020

(65) Prior Publication Data
US 2021/0378101 A1    Dec. 2, 2021

(30) Foreign Application Priority Data
Jul. 30, 2018 (FR) ..................... 18 57094

(51) Int. Cl.
*H05K 1/18* (2006.01)
*H05K 1/11* (2006.01)
(Continued)

(52) U.S. Cl.
CPC ............ *H05K 1/189* (2013.01); *H05K 1/118* (2013.01); *H05K 1/186* (2013.01); *H05K 3/284* (2013.01); *H05K 3/32* (2013.01); *A61B 2562/164* (2013.01)

(58) Field of Classification Search
CPC ........ H05K 1/189; H05K 1/118; H05K 1/186; H05K 3/284; H05K 3/32; A61B 2562/164
(Continued)

(56) References Cited

U.S. PATENT DOCUMENTS

2006/0097373 A1    5/2006 Ito
2006/0207088 A1    9/2006 Yamano
(Continued)

FOREIGN PATENT DOCUMENTS

WO    WO 2013/082537 A1    6/2013

OTHER PUBLICATIONS

U.S. Appl. No. 16/514,490, filed Jul. 17, 2019, US/2020/0023368 A1, Jean-Charles Souriau et al.
(Continued)

*Primary Examiner* — Binh B Tran
(74) *Attorney, Agent, or Firm* — Oblon, McClelland, Maier & Neustadt, L.L.P.

(57) ABSTRACT

A flexible electronic structure includes a first film, made of a first polymer or glass, and a second film, made of a second polymer, in which at least one electronic component is arranged. The second film covers the first film. The flexible electronic structure also includes at least one electrically conductive track arranged between the first film and the second film, and each electrically connected to one of the electronic components, by a respective interconnection element. Optionally, the flexible electronic structure includes a third film, made of a third polymer or glass, covering the second film. The interconnection element is arranged near
(Continued)

the neutral plane of the structure, and the structure includes at least one compensation layer, so as to position the neutral plane at a desired location.

21 Claims, 6 Drawing Sheets

(51) Int. Cl.
*H05K 3/28* (2006.01)
*H05K 3/32* (2006.01)

(58) Field of Classification Search
USPC .......................................................... 361/749
See application file for complete search history.

(56) References Cited

U.S. PATENT DOCUMENTS

| | | | |
|---|---|---|---|
| 2007/0134849 A1 | 6/2007 | Vanfleteren et al. | |
| 2009/0002973 A1* | 1/2009 | Watanabe .............. | H05K 1/023 |
| | | | 361/820 |
| 2009/0107703 A1 | 4/2009 | Abe et al. | |
| 2011/0242780 A1 | 10/2011 | Watanabe et al. | |
| 2012/0140424 A1* | 6/2012 | Sato ..................... | G02F 1/13454 |
| | | | 257/E29.273 |
| 2014/0003015 A1 | 1/2014 | Watanabe et al. | |
| 2014/0306250 A1 | 10/2014 | Gardner et al. | |
| 2015/0157862 A1 | 6/2015 | Greenberg et al. | |
| 2017/0186533 A9 | 6/2017 | Wang | |
| 2018/0027651 A1 | 1/2018 | Lim et al. | |
| 2018/0042107 A1 | 2/2018 | Yosui | |
| 2018/0256099 A1* | 9/2018 | Li ........................ | A61B 5/6815 |
| 2019/0239345 A1 | 8/2019 | Lim et al. | |

OTHER PUBLICATIONS

Suo, Z. et al., "Interface crack between two elastic layers," International Journal of Fracture, 1990, vol. 43, pp. 1-18.

Eberl, C. et al., "Mechanical Characterization of Coatings Using Microbeam Bending and Digital Image Correlation Techniques," Experimental Mechanics, DOI 10.1007/s11340-008-9187-4, total pp. 14.

International Search Report dated Sep. 30, 2019 in PCT/FR2019/051865 filed on Jul. 29, 2019, 3 pages.

French Search Report with English translation of categories dated Jul. 24, 2019 in French Application No. 18 57094 issued on Jul. 30, 2018, 3 pages.

\* cited by examiner

FLEXIBLE ELECTRONIC STRUCTURE AND METHOD FOR PRODUCING SAME

TECHNICAL FIELD AND PRIOR ART

The present invention relates to a flexible electronic structure, integrating one or more electronic components, capable of being deformed and being able to be placed, on a non-planar surface such as the skin or an object.

The present invention also relates to the method for preparing such a structure.

Flexible electronic structures, also called flexible electronic devices, can integrate electronic components such as communication means (antenna), integrated circuits, actuators, batteries, RFID chips or else passive components.

To produce such structures, it is possible to transfer electronic components to a bendable printed circuit of polyester, polyimide, polytetrafluoroethylene or polyetheretherketone type. Printed circuits comprise metal tracks and interconnection pads to which the components are attached by brazing, using fusible materials or by bonding, for example. The components are attached on the surface of the flexible film, either with the active face down or with the active face up, and interconnected using electrically conductive wires ("wire bonding"). Generally, the metal tracks are covered with a solder resist or a dielectric film which is used as an anti-soldering mask and an isolating and protective layer against corrosion and damage.

However, since the electronic components are often thick and stiff, the bending stresses in the structure place a heavy strain on the bonding, soldering or brazing interfaces, which end up breaking.

To overcome this problem, one solution consists in using thinner electronic components to make them more flexible. For example, document US-A-2007/0134849 proposes a device ("Ultra-Thin Package" (UTCP)) wherein a chip has a thickness of 10 µm to 50 µm. To produce the device, the chip, after being thinned, is attached on a stiff substrate, active face up (opposite the substrate). The substrate can be glass covered with a 20 µm thick layer of polyimide. The chip is, for example, attached on the substrate by means of a bicyclobutane benzocyclobutene (BCB) or polyimide layer. Once attached, the chip is covered with another 20 µm thick polyimide layer. The upper polyimide layer is then etched in order to be able to make the contact point through the upper layer and the metal tracks are produced on the surface of the structure. The flexible structure is finally separated from the stiff substrate. For example, for 20-30 µm thick chips, which are encapsulated between two 20 µm thick polyimide layers, the final flexible structure has a thickness of 60-70 µm.

However, this structure can only be achieved with ultra-thin chips (here with a thickness less than 50 µm). However, the components available on the market rarely have such thin thicknesses, and it is not possible, from an industrial point of view, to individually thin each electronic component in order to then be able to transfer it into a flexible structure. In addition, the metal tracks and the contact points are subjected to bending and torsional stresses, which can weaken them and thus reduce the lifetime of the structure.

Document US-A-2006/0097373 proposes an electronic device wherein an ultra-thin semiconductor chip is bonded to a flexible substrate. The semiconductor chip incorporates a connection pad. The latter is flush with the upper or lower surface of the chip, at the neutral plane of the electronic device. This arrangement allows to limit constraints at the electrical connection of the semiconductor chip, when the device is folded.

A purpose of the present invention is to provide a flexible structure having an even improved lifetime compared to the prior art, and in particular better resistance to mechanical bending stresses.

Another purpose of the present invention is to provide a method for producing such a structure, which is easy to implement, which does not require each component to be individually thinned before it is placed in the structure, and which can be applied on an industrial scale.

DESCRIPTION OF THE INVENTION

These purposes are achieved with a flexible electronic structure comprising:
- a first film, made of a first polymer or of glass,
- a second film, made of a second polymer, wherein at least one electronic component is disposed, the second film covering the first film,
- at least one electrically conductive track disposed between the first film and the second film, and each electrically connected to at the least one electronic component, by a respective interconnection element,
- optionally a third film made of a third polymer or of glass, covering the second film.

Each interconnection element is disposed near the neutral plane of the structure, that is to say passing through a plane whose distance from the neutral plane is less than or equal to 20% of the total thickness of the structure.

According to the invention, the flexible electronic structure further comprises at least one discontinuous compensation layer, formed of one or more discrete portions which each extend opposite one of the at least one electrically conductive track or opposite one of the at least one electronic component.

The compensation layer may be formed distinct from the first, second and third films, consisting of one or more discrete portions made of a material distinct from the respective material forming each of said films.

Alternatively, the compensation layer may be glass and formed integrally with the third film when it is glass. In other words, the compensation layer then forms one or more local extra thicknesses in a glass layer forming both the third film and the compensation layer. Still in other words, a glass layer forming both the third film and the compensation layer has a surface topography, on the side opposite the second film, with one or more plateaus which form the compensation layer.

Flexible means that the structure is bendable, that is to say that it can undergo bending with a radius of curvature less than or equal to 1000 mm and preferably less than or equal to 200 mm, without breaking. The presence of the two or three polymer or glass films ensures the flexibility of the device. In particular, the second film advantageously has a Young's modulus less than or equal to 5000 MPa, and preferably less than or equal to 3500 MPa. Likewise, the first film and the third film, when they are made of polymer, each have a Young's modulus less than or equal to 5000 MPa, and preferably less than or equal to 3500 MPa. When the first, respectively the third film is made of glass, then it has a Young's modulus greater than 50 GPa, implying the use of smaller thicknesses. For each film, and depending on the material used, a person skilled in the art will know how to determine a range of thicknesses allowing the above-mentioned condition of bending without breaking to be achieved.

When the structure is subjected to a bending stress, the structure undergoes compressive stresses in its upper part (reduction of the upper surface) and tensile stresses in its lower part (increase of the lower surface), or vice versa depending on the bending direction. In the middle of the structure, the compressive and tensile stresses compensate each other, creating a surface where the mechanical stresses related to the bending are zero. This surface is called the neutral plane, or neutral fiber. Each interconnection element of the electronic component being disposed near this neutral plane, it is subjected to little stress during bending. The bonding, soldering and/or brazing interfaces are thus preserved.

The proximity of the neutral plane here denotes a zone where the compressive and tensile stresses are very low, that is to say in a zone corresponding to ±20%, preferably ±10%, even more preferably ±5%, or even ±2%, of the total thickness of the structure relative to this neutral plane. In other words, each interconnection element passes through a plane parallel to the neutral plane, located at a distance from the latter less than or equal to 20% of the total thickness of the structure, preferably less than or equal to 10% of this total thickness, even more preferably less than or equal to 5% or even less than or equal to 2% of this total thickness. The distances are measured, in one direction or the other, along an axis orthogonal to the plane of the flexible electronic structure. Each electrically conductive track, connected to one of the interconnection elements, is also at the center of the structure. It is not disposed on the surface of the structure. It is close to the neutral plane, so that it is not damaged during mechanical stress, such as during bending stresses.

The position of each interconnection element and each electrical track relative to the neutral plane can be controlled by adjusting the thickness of the first film and/or the second film and/or the third film.

According to the invention, the flexible electronic structure further includes at least one compensation layer, which has the function of locally displacing the position of the neutral plane along the axis of the thickness of the structure. The neutral plane can thus be positioned at a desired location, as close as possible to each interconnection element. The compensation layer consists of discrete portions which each extend opposite one of the at least one electrically conductive track, respectively opposite one of the at least one electronic component. Opposite means that the portion of the compensation layer is facing the electrically conductive track or facing the component. Preferably, an orthogonal projection of the portion of the compensation layer, in the plane of the electrically conductive track, respectively of the component, does not project laterally relative to said track, respectively relative to said component. The portion of the compensation layer may have the same surface area or different surface area, the same pattern or different pattern, as the electrically conductive track or as the electronic component. The surface area here designates the area of the section in a plane parallel to the plane of the films. Each compensation layer forms a structured film, extending in a plane parallel to the plane of the flexible electronic structure, and providing non-uniform compensation over the entire extent of the flexible electronic structure. In other words, the compensation is only local along the extent of the flexible electronic structure.

The compensation layer is made, for example, of a material whose Young's modulus is close to that of the electrical track, in order to have equivalent mechanical properties (in particular stiffness). More generally, the features (material, surface area, thickness, pattern) of the compensation layer are selected so as to locate each connection element, and if possible each electrically conductive track, close to the neutral plane. According to an advantageous embodiment, the second film includes several electronic components of different surface areas, and one of the at least one compensation layer comprises a portion covering the electronic component of smallest surface area so as to stiffen it. Preferably, said compensation layer has a greater stiffness than that of the electronic component with a smaller surface area, that is to say it has a Young's modulus greater than that of the electronic component with a smaller surface area. Such a compensation layer allows to maintain the neutral plane as close as possible to the embedded electronic component, by locally stiffening the structure. Here also, the surface area of the electronic component designates the area of a section of this component in a plane parallel to the plane of the first, second and optional third films.

The at least one of the other electronic components has a larger surface area, and is not covered with a portion of the compensation layer. Preferably, the compensation layer consists of the single portion covering the component of smallest surface area.

Alternatively, a respective portion of the compensation layer covers each electronic component so as to stiffen it. Said portions can have different thicknesses.

Advantageously, one of the at least one compensation layer is disposed between the second film and the third film, consisting of portion(s) each located opposite one of the at least one electrically conductive track.

Additionally or alternatively, one of the at least one compensation layer covers the third film, and consists of portion(s) each located opposite one of the at least one electrically conductive track. Said compensation layer then extends on the side of the third film opposite the electronic component.

According to another variant, one of the at least one compensation layer consists of portion(s) each located opposite one of the at least one electrically conductive track, the first film being disposed between the electrically conductive track and the compensation layer. In other words, the compensation layer is under the first film, on the side opposite the at least one electronic component.

The structure according to the invention can comprise two compensation layers which are separate from each other. For example, the two compensation layers each consist of portions each located opposite an electrically conductive track, so that the same electrically conductive track is aligned with two portions belonging to two separate compensation layers. The two compensation layers can be called first compensation layer, for one, and additional compensation layer, for the other. The additional compensation layer will be positioned by the person skilled in the art depending on the position of the first compensation layer. The additional compensation layer can be positioned according to one of the variants described above. For example, the first compensation layer can be disposed between the second film and the third film, and the additional compensation layer can be positioned under the first film. Alternatively, two compensation layers may consist, for one, of portions each located opposite an electrically conductive track, and for the other of portions each located opposite an electronic component.

Advantageously, the at least one compensation layer is made of the same material as the at least one electrically conductive track.

Advantageously, the electronic component has a thickness less than 350 μm, and preferably less than 100 μm, even more preferably less than 70 μm in order to maintain the flexibility properties of the structure. It can, for example, have a thickness of 20 μm to 50 μm or else of 70 μm to 100 μm.

Advantageously, a respective metal via, electrically connected to one of the at least one electrically conductive track, extends in the first film so as to connect one of the at least one electronic component through the first film, the metal via being filled with the second polymer. The electrically conductive track can thus be electrically interconnected with the outside thanks to the metal via.

The structure according to the invention may further include at least one metal tip, each electrically connected to one of the at least one electrically conductive track by means of the corresponding via, and protruding from the first film on the side opposite to said electrically conductive track, the tip being filled with the second polymer.

The structure may comprise at least one sealing trench, each surrounding one of the at least one electronic component, the polymer of the third film filling the sealing trench.

Advantageously, the first polymer, the third polymer and, preferably, the second polymer, are identical.

Advantageously, at least one through-hole extends in the first film and/or in the third film, each so as to make one of the at least one electronic component accessible. The through-holes form vents that allow components to be exposed to the surrounding atmosphere. This may be of interest for example for applications where the flexible device must interact with its external environment, such as for example to measure the water loss of a person.

Advantageously, the electronic component is an integrated circuit with specific application, a sensor, an actuator, a stimulator, a microbattery, or an RFID chip.

Many components of different kinds can be integrated.

The pursued purpose is also achieved by a method for preparing a flexible electronic structure as defined above, said method comprising the following successive steps:
a) providing a substrate,
b) forming the first film made of a first polymer or of glass, on the substrate,
c) forming the at least one electrically conductive track on the first film,
d) forming the second film made of a second polymer wherein at least one electronic component is disposed, each electronic component being electrically connected with one of the at least one electrically conductive track, by a respective interconnection element,
e) optionally, forming the third film made of a third polymer or of glass,
f) separating the substrate from the flexible electronic structure.

The method of the invention also comprises at least one step of forming at least one compensation layer.

The method of the invention is simple to implement. It uses conventional methods used in microelectronics and in the field of assembly and encapsulation of electronic components. The various polymer or glass films can be formed in a temperature range from room temperature (20-25° C.) up to, for example, 350° C., depending on the nature of the polymers. The method is easily transferred to an industrial scale.

Advantageously, step d) is carried out by:
forming a full film made of the material of the second film,
etching the full film, so as to form at least one cavity, each cavity making one of the at least one electrically conductive track accessible,
transferring a respective electronic component into each cavity and connecting each electronic component with at least one of the at least one electrically conductive track, each connection being made through a respective interconnection element,
optionally, thinning the at least one of the at least one electronic component.

According to a variant, step d) is carried out by:
transferring and connecting at least one electronic component, each on at least one of the at least one electrically conductive track, each connection being made by means of a respective interconnection element,
optionally, thinning the at least one electronic component.
forming the second film on the at least one electronic component and on the first film.

Thinning is implemented by etching or grinding. In both variants, the optional thinning is carried out during preparation of the flexible structure, over the entire structure. The thinning of an electronic component previously positioned at its final location in the structure simplifies the method according to the invention, in comparison with a thinning prior to transfer on the final structure. When the flexible structure includes several electronic components, the thinning of the components is carried out collectively. Collective thinning is easier to achieve than a plurality of separate thinnings on single elements, as in the prior art. In the first variant, the second film can be used as a layer for stopping an etching performing the thinning.

Advantageously, between step a) and step b), a sacrificial layer is deposited on the support and, during step f), the sacrificial layer is etched to separate the support from the flexible electronic structure.

Advantageously, before step b), one of the at least one compensation layer is formed on the substrate, and/or, after step d), one of the at least one compensation layer is formed on the second film and/or, after step e), one of the at least one compensation layer is formed on the third film.

Advantageously, the first polymer, respectively the third polymer, is a polyimide, a polysiloxane, a parylene, a thermoplastic polymer.

The substrate advantageously includes recesses in the shape of a tip, forming indentations to form metal tips protruding from the first film, on the side opposite the electrically conductive track.

BRIEF DESCRIPTION OF THE DRAWINGS

The present invention will be better understood on the basis of the description which follows and the appended drawings wherein.

The different parts in the figures are not necessarily shown with a uniform scale, to make the figures more readable.

The various possibilities (variants and embodiments) must be understood as not being mutually exclusive and can be combined with each other.

DETAILED DESCRIPTION OF PARTICULAR EMBODIMENTS

First, reference is made to FIGS. 1 to 10 which show a flexible electronic structure 100 according to various embodiments.

The person skilled in the art will be able to combine the various embodiments with each other in different ways.

Figure 1A:
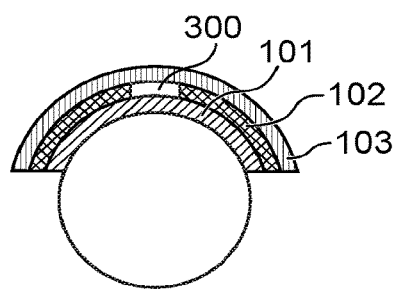
FIG. 1A is a schematic sectional and side representation of a flexible electronic structure wound around a curved surface.

Flexible Electronic Structure:

As shown in FIG. 1A, the structure 100 is bendable, for example it can be wound around a curved surface without any breaks or cracks in the structure. The structure is conformable. It can be bent until having a radius of curvature less than or equal to 1000 mm, preferably less than or equal to 200 mm, this radius of curvature being able to reach 10 mm, and even 5 mm, or even up to 2 mm without the structure 100 being damaged.

The structure 100 comprises in particular a first film 101, a second film 102, an optional third film 103, at least one electronic component 300 electronically connected to at least one respective electrically conductive track 200, and at least one compensation layer 500.

For greater readability, only the first film 101, the second film 102 and the third film 103 as well as an electronic component 300 are shown in FIG. 1A.

The flexible electronic structure 100 can be directly worn by a person, for example on a wrist, an arm or a torso. The electronic structure 100 can be used for medical or welfare applications for example. By way of illustration, the structure 100 can be an integral part of a device for measuring temperature, heart rate, actimetrics, or degassing of the skin (sweat), or else of an electrical or optical stimulation device, or a drug delivery device. The structure can be wound around a catheter, for example. The flexible electronic structure 100 can be directly transferred to any type of object with more or less round shapes.

The structure 100 has a thickness comprised between 20 µm and 400 µm, preferably between 50 µm and 150 µm and even more preferably of the order of 100 µm.

Throughout the text, the term "thickness" refers to a dimension along an axis perpendicular to the stack of polymer or glass films.

The plane of the flexible electronic structure is also defined as being a plane orthogonal to the axis of the thickness, parallel to which each of the polymer or glass films extend.

The neutral plane of the structure (also called neutral fiber) is represented by the dotted line PN in the different figures. The mechanical stresses during bending are minimal in this plane and the elements disposed in this plane keep their integrity. According to the invention, the neutral plane is at the electrical connections between the electronic components 300 and the electrically conductive tracks 200.

The First Film 101:

The first film 101, also called the lower film, is bendable. Bendable means that the film can undergo bending with a radius of curvature less than or equal to 1000 mm and preferably less than or equal to 200 mm without breaking.

The first film 101 is made of polymer or of glass. The term "polymer" is preferably understood here and below to mean a homopolymer or a copolymer. By way of illustration, the polymer can be selected from the following non-exhaustive list (the Young's modulus has been indicated in brackets): a polyimide (from 2 to 8 GPa, for example 3.2 Pa), a polymerized siloxane (from 0.05 to 0.5 GPa, for example 0.15 GPa) such as silicone (less than 0.1 GPa) or a siloxane polymer SINR™, parylene (2.4 to 3 GPa), a thermoplastic such as polyethylene (200-700 MPa), polyethylene terephthalate or PET (2800-3100 MPa), poly(ethylene naphthalate) or PEN (500-1500 MPa), etc. Its thickness ranges from 5 µm to 150 µm, preferably from 10 µm to 75 µm, and even more preferably from 10 µm to 30 µm. Note that when the first film is made of glass, it has a higher Young's modulus (from 69 to 72 GPa) so that it then has a thickness located in the lower part of the thickness ranges indicated above.

The Second Film 102:

The second film 102 (also called an inner film) is made of a bendable polymer material. It is advantageously made of a material able to fill vias or trenches. This can be a thermoplastic or a siloxane polymer SINR™. Alternatively, it can also be a polyimide, a polymerized siloxane such as silicone or parylene. The thickness of this film ranges from 5 µm to 150 µm, preferably from 10 µm to 75 µm, and even more preferably from 10 µm to 30 µm.

The Third Film 103 (Optional):

The third film 103 (also called the upper film) is made of a bendable material. The material of the third film is a polymer or a glass film. This can be a polyimide, a polymerized siloxane such as silicone or siloxane polymer SINR™, a thermoplastic, parylene or a glass. It will advantageously be made of a material able to fill vias or trenches. The thickness of this film ranges from 5 µm to 150 µm, preferably from 10 µm to 75 µm, and even more preferably from 10 µm to 30 µm.

Figure 1B:
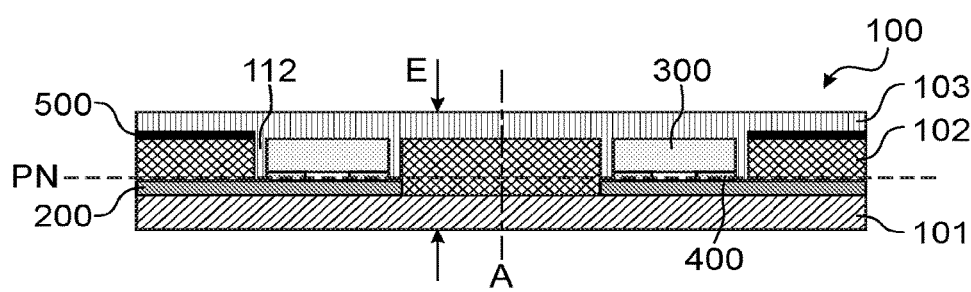
FIG. 1B is a schematic sectional and side representation of a flexible electronic structure according to a first embodiment of the invention.
Figure 2:
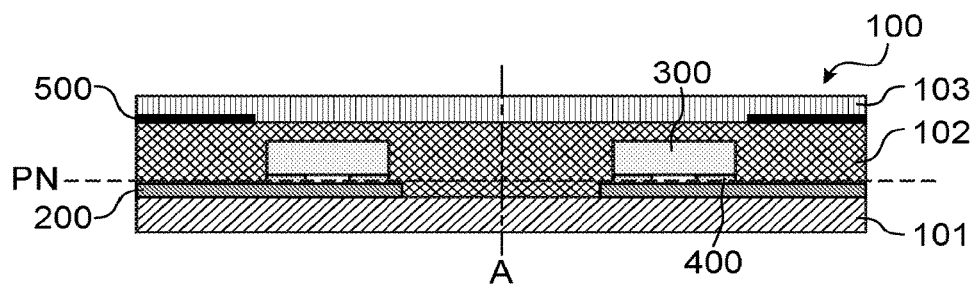
FIG. 2 is a schematic sectional and side representation of a flexible electronic structure according to a second embodiment of the invention.

As shown in FIGS. 1A and 1B, the second film 102 may have a thickness identical to that of the component 300 to be encapsulated. Identical means that the difference in thickness is less than or equal to 30% of the thickness of the component 300 (thickness in the flexible structure according to the invention, after optional thinning).

According to variants, the second film 102 may have a thickness smaller or greater (FIG. 2) than the thickness of the electronic component.

When the second film 102 has a thickness greater than that of the electronic component 300 and covers it, the structure may not comprise a third film 103. For example, in this embodiment, the second film 102 may have a thickness approximately twice as large as that of the first film 101, so as to maintain the neutral plane at the level of the connection between the electronic component 300 and the electrically conductive track 200, without the need to add a third film above the second film.

The three films (first 101, second 102 and third 103 films) can be made of different or identical materials.

Preferably, the first film 101 and the third film 103 are made of the same material. The mechanical properties of the structure 100 (flexibility in particular) are thus better balanced. The material of the first film 101 and/or of the third film 103 can be biocompatible materials, for example polysiloxane.

Figure 3:
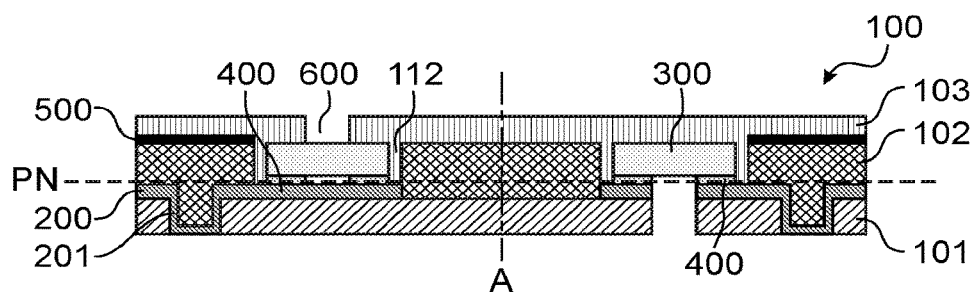
FIG. 3 is a schematic sectional and side representation of a flexible electronic structure according to a third embodiment of the invention.
Figure 4:
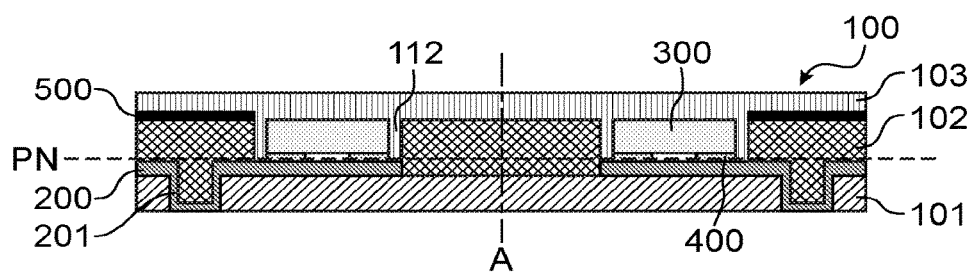
FIG. 4 is a schematic sectional and side representation of a flexible electronic structure according to a fourth embodiment of the invention.

In a particular embodiment, shown in FIG. 3, through-holes 600 are disposed in the first film 101, and/or in the third film 103 or the second film, so as to make each one of the electronic components 300 accessible from the outside. The through-holes 600 form vents which allow the components 300 to be exposed to the surrounding atmosphere. This may be of interest for example for applications where the flexible device must interact with its external environment, such as for example to measure the water loss of a person.

Electrical Tracks 200:

The electrically conductive tracks 200, or electrical tracks 200, are disposed within the structure 100, between the first film 101 and the second film 102, as close as possible to the neutral plane.

The electrical tracks 200 are electrically conductive. They can be metallic, for example Cu, Ag, Au, Al, W, Ni, Pt, Ti or Ru. In the case of a structure which has to be biocompatible, for example for medical applications, a noble metal will be selected, such as for example, gold or platinum. The electrical tracks 200 can also be made from an ink loaded with metal particles like those used in organic electronics. The thickness of the tracks 200 may be from 50 nm to 5 µm, and preferably from 100 nm to 2 µm.

As shown in FIGS. 3 to 9, vias 201 can be made in the first film 101. The vias pass through the first film 101 and are metallized (that is to say covered with an electrically conductive metal layer). The material of the second film 102 extends into the vias 201 and fills the vias 201, which improves the mechanical holding of the structure 100.

Figure 9:
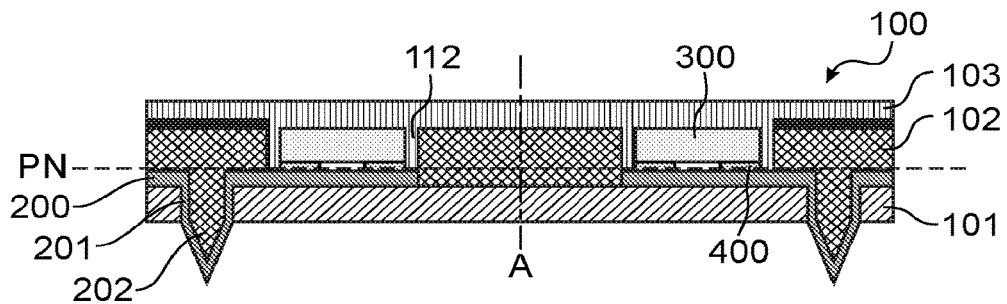
FIG. 9 is a schematic sectional and side representation of a flexible electronic structure according to a ninth embodiment of the invention.

As shown in FIG. 9, the flexible structure 100 may also comprise one or more metal tips 202, or protrusions, protruding from the first film 101 in the direction opposite the electrically conductive tracks. The tips 202 are connected to the electrical tracks 200 by the vias 201. In particular, each tip 202 extends in the continuity of a via 201, on the side opposite the electrical tracks, under the first film 101. The tips 201 are filled. each by the material of the second film 102.

The thicknesses of the films mentioned above do not take into account any vias or any tips.

Figure 10:
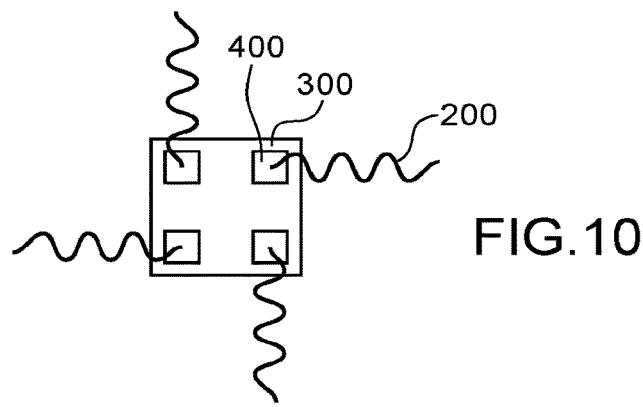
FIG. 10 is a schematic representation of an electronic component, seen from above, connected to electrically conductive tracks according to a particular embodiment of the invention, FIGS. 11A to 11M schematically show various steps of the method for producing a flexible electronic structure, according to a particular embodiment of the invention, FIGS. 12A to 12B schematically show various steps of the method for producing a flexible electronic structure, according to another particular embodiment of the invention, FIGS. 13A to 13B schematically show various steps of the method for producing a flexible electronic structure, according to another particular embodiment of the invention.

In a variant shown in FIG. 10, the electrical tracks 200 are in the form of a coil so as to give them a certain elasticity and therefore to mechanically contribute to the flexible behavior of the structure 100. During bending stresses, the electrical tracks may stretch. The arrangement of the various tracks of the same flexible structure 100 advantageously has a symmetry such as that illustrated in FIG. 10, to participate in a symmetry of the structure 100. Here, it is an axial symmetry centered on the geometric center of the structure 100.

The Integrated Electronic Component 300:

The component 300 integrated into the structure 100 can be selected from an ASIC (that is to say an integrated circuit with specific application), a sensor, an actuator, a stimulator, a battery, an RFID (that is to say radiofrequency identification) chip, or a passive component. The face of the component in contact with the electrical connection pads 400 is facing the first film 101, in order to be able to electrically connect each connection pad to one of the electrically conductive tracks 200. The component 300 is, for example, made of silicon.

Once integrated into the structure, the electronic component 300 has a thickness comprised between a few tens, even a few hundreds of micrometers, and around ten micrometers. It has for example a thickness comprised between 10 µm and 350 µm. Its thickness is for example comprised between 100 µm and 150 µm. Alternatively, it has a thickness less than 100 µm, and preferably less than 50 µm, for example from 20 µm to 50 µm, to maximize the flexibility properties of the structure.

As shown in FIGS. 1B and 3 to 9, the electronic component 300 is preferably surrounded by a sealing trench 112. The sealing trench 112 separates the second film 102 from the component 300. The width of the trench 112 can range from 10 µm to 500 µm, and preferably from 30 µm to 100 µm. The sealing trench 112 is filled with the material of the third film 103 if it exists, otherwise with the material of the second film 102.

The structure 100 can comprise one or more components 300, of the same surface area or of different surface areas, of the same nature or of different natures. For example, it is possible to have an RFID chip and a sensor.

Preferably, but optionally, and as shown in FIGS. 1A to 9, the structure 100 comprises several components 300 and has a plane of symmetry (plane A), or an axis of symmetry (axis A). This symmetry will be respected as best as possible to control the position of the neutral plane. The plane A, respectively the axis A passes through the center of the structure 100, between at least two electronic components, and extends orthogonal to the planes of the films 101, 102 and 103.

The Interconnection Element 400 Between the Electrically Conductive Track 200 and the Integrated Electronic Component 300:

The interconnection element 400, or interconnection pad, electrically and mechanically connects each electrically conductive track 200 with a component 300. The interconnection element 400, the electrical track 200 and the electronic component 300 are integral.

A same electronic component 300 can be connected to one or more electrical tracks 200. For example in FIG. 10, the component 300 is connected to four electrically conductive tracks 200 via four interconnection elements 400.

The interconnection element 400 is electrically conductive. For example, it can be made from fusible brazing based on tin or lead, for example, such as SnAg, SnPb or SnAgCu. It can also be a bump, preferably gold, better known as a "stud bump" or "accu bump". It can also be a conductive adhesive. It can also be a conductive ink, for example silver-based conductive ink. It can also be part of a conductive element, such as a metal pillar, called a micro-insert, micro-tube (or pilar), according to the techniques used to connect the electronic component 300 to the electrical track 200.

The interconnection element 400 has a thickness ranging from 0.5 µm to 70 µm. Preferably, the interconnection element has a thickness greater than 10 µm only if it is a "stud bump".

According to the invention, the interconnection element 400 passes through a plane whose distance from the neutral plane is less than or equal to 20% of a total thickness E of the structure 100. Said distance is measured in one direction or the other, along an axis orthogonal to the plane along which extends the flexible structure.

When the interconnection element 400 is a "stud bump" type bump, it has a high thickness, greater than 10 µm. Such an interconnection element 400 is initially attached to one among the electrical track 200 and the component 300, by fusion, then attached to the other among the electrical track 200 and the component 300, by simple thermo-compression. The attachment made by thermo-compression is the most fragile of the two attachments. Consequently, the face of the interconnection element which is attached by thermo-compression is positioned closest to the neutral plane. The thermo-compression attachment can be at the interface between the interconnection element 400 and the electrical track 200, or at the interface between the interconnection element 400 and the electronic component 300.

By way of illustration only, in the case of a stack comprising an upper layer and a lower layer, stacked on top of each other, and homogeneous, the position of the neutral plane can be calculated with the formula described in the respective articles of Suo and al. ("Interface crack between two elastic layers", International Journal of Fracture 43: 1-18, 1990) and Eberl and al. ("Mechanical Characterization of Coatings Using Microbeam Bending and Digital Image Correlation Techniques", Experimental Mechanics DOI 10.1007/s11340-008-9187-4):

$$\frac{h_0}{h_{low}} = \frac{1 + \frac{2.E_{up}.h_{up}}{E_{low}.h_{low}} + \frac{E_{up}.h_{up}^2}{E_{low}.h_{low}^2}}{2.\left(1 + \frac{E_{up}.h_{up}}{E_{low}.h_{low}}\right)}$$

with:
$h_0$ the position of the neutral plane,
$h_{up}$ and $E_{up}$, respectively, the thickness and Young's modulus of the upper layer,
$h_{low}$ and $E_{low}$, respectively, the thickness and Young's modulus of the lower layer.
For example, in the case of a stack having:
an upper silicon layer with the following features: $h_{up}$=45 µm, $E_{up}$=130 GPa,
a lower polymer layer with the following features: $h_{low}$=100 µm, $E_{low}$=2.5 GPa,
the position of the neutral plane $h_0$ is at 120 µm, that is to say the neutral plane is in the upper layer.

The displacement of the neutral plane can be achieved, for example, by adding a metal layer of nickel (10 µm thick and 214 GPa of Young's modulus) or of ruthenium (5 µm thick and 447 GPa of Young's modulus), under the stack, that is to say in contact with the lower layer. The new position of the neutral plane is, respectively, at 110 µm and at 105 µm.

The Compensation Layer 500:
As shown in the figures, the structure further comprises a compensation layer 500, also called a compensating layer, to locally stiffen the structure in its most flexible region, and thus change the position of the neutral plane of the structure.

The compensation layer 500 is a layer consisting of discrete portions spaced apart from each other.

The compensation layer 500 allows to stiffen, for example, the upper part of the structure just like the at least one electrical track 200 stiffens the lower part of the structure (FIGS. 1A to 5B). It can also allow to stiffen the lower part of the structure even more (FIG. 6). The compensation layer 500 and the at least one electrical track 200 preferably have the same Young's modulus. Alternatively, a material with a higher Young's modulus than that used in the track 200 can be used for the compensation layer 500, so as to reduce the thickness of the compensation layer 500.

The person skilled in the art will select the materials and thicknesses of the at least one electrical track 200 and the compensation layer 500 so as to locate the at least one interconnection element 400 as close as possible to the neutral plane. The compensation layer 500 and the at least one electrical track 200 can be of the same material and/or have the same thickness.

For example, the compensation layer 500 is metal. It can be made of Cu, Ag, Au, Al, W, Ni, Pt or Ti. For applications requiring biocompatibility, a noble metal will be selected, such as, for example, gold or platinum.

It can also be a loaded ink, such as those used in organic electronics, or a polymer.

The thickness of the compensation layer may be comprised between 100 nm and 10 µm, for example comprised between 0.5 µm and 10 µm or between 100 nm and 5 µm, and preferably between 0.5 µm and 2 µm.

According to a first embodiment, the compensation layer 500 consists of portion(s) each disposed above one of the electrically conductive tracks 200, each opposite one of the electrical tracks 200. The compensation layer 500 then extends on the side of the second film 102 opposite to the first film 101.

According to a first variant shown in FIGS. 1B to 4, the structure 100 comprises the third film 103, and the compensation layer 500 and the at least one electrically conductive track 200 are disposed on either sides of the second film 102. The compensation layer 500 then extends directly over the second film 102, on the side opposite the first film 101. "Directly" means in direct physical contact, without an interlayer.

Figure 5A:
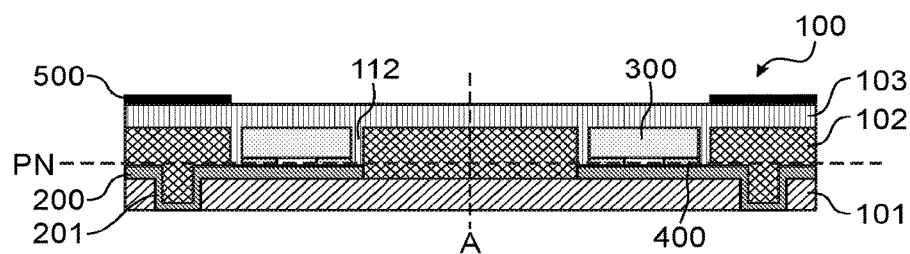
FIGS. 5A and 5B are schematic sectional and side representation of two variants of a flexible electronic structure according to a fifth embodiment of the invention.
Figure 5B:
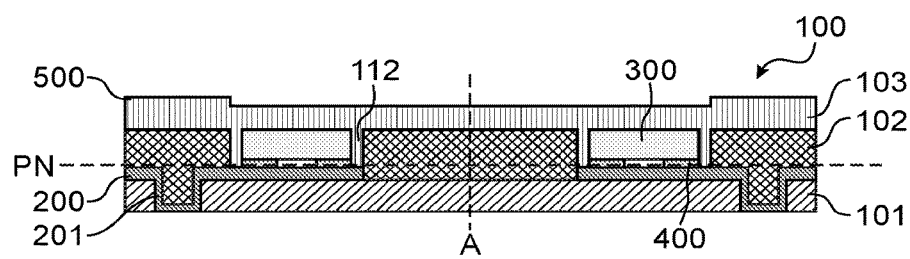
Figure 6:
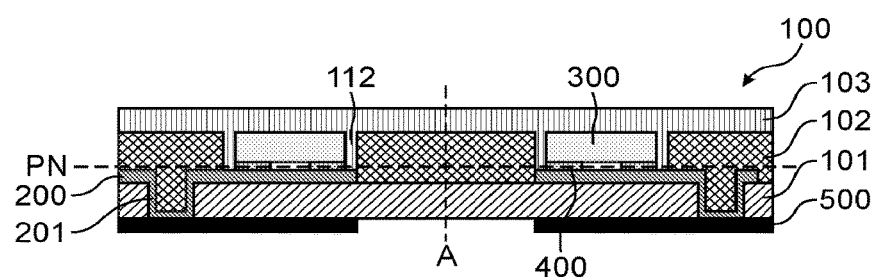
FIG. 6 is a schematic sectional and side representation of a flexible electronic structure according to a sixth embodiment of the invention.

According to another variant, as shown in FIGS. 5A and 5B, the structure 100 comprises the third film 103, and the compensation layer 500 and the at least one electrically conductive track 200 are disposed on either sides of the assembly formed by the second film 102 and the third film 103. In other words, the compensation layer 500 is disposed directly on the third film 103, on the side opposite to the component 300. Preferably, and as shown in FIGS. 5A and 5B, the compensation layer 500 consists of portion(s) not covering the electronic component 300. Alternatively, the first compensation layer 500 may consist of portion(s) each having the same size as the electrically conductive track 200 located opposite thereto. It is possible, advantageously, to select elements of the same shape.

In the variant illustrated in FIG. 5A, the compensation layer 500 consists of a material distinct from that of the third film.

In the variant illustrated in FIG. 5B, the compensation layer 500 consists of local extra thicknesses in a glass layer which forms both the third film 103 and the compensation layer 500. For example, there is a thickness of the order of 10 µm just above the electronic components 300, and a thickness of approximately 100 µm just above the tracks 200. In any event, the glass thickness just above the tracks is at least 5 times greater than the glass thickness just above the tracks 200. This variant is produced by etching a layer of glass deposited on the second film 102 (chemical etching and lithography, for example).

In both variants, the third film is delimited by a flat surface, on the side opposite to the second film.

According to another variant, not shown, the structure 100 does not include the third film 103, and the compensation layer 500 extends directly over the second film 102, formed of portion(s) each located opposite one of the electrical tracks 200. Preferably, each portion of the compensation layer 500 does not cover the at least one component 300.

According to a second embodiment as shown in FIG. 6, the compensation layer 500 is disposed below the first film 101, consisting of portion(s) each located opposite one of the electrical tracks 200. The compensation layer 500 then extends on the side of the first film 101 opposite to the second film 102. Preferably, the compensation layer 500 consists of portion(s) which each extend up to below one of the electronic components 300. According to a variant not shown, the compensation layer is disposed below the first film 101, consisting of portion(s) each located opposite one of the electronic components 300.

In each of these embodiments, the compensation layer 500, when projecting relative to the stack of films 101, 102, 103, is not taken into account in determining the total thickness of the structure 100.

According to a variant not shown, the structure 100 can comprise at least one additional compensation layer which can be made of the same material as the at least one electrically conductive track 200.

Figure 7:
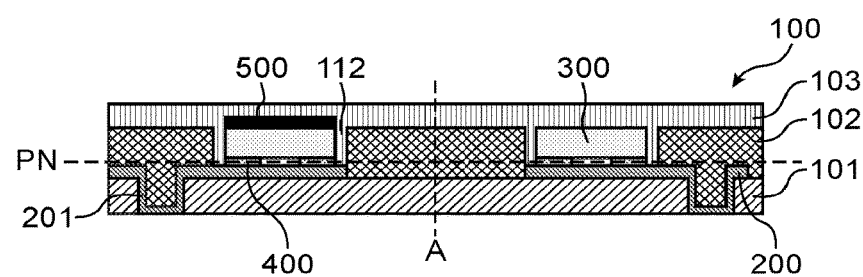
FIG. 7 is a schematic sectional and side representation of a flexible electronic structure according to a seventh embodiment of the invention.

When the structure 100 comprises at least two components 300 of different surface areas, the position of the neutral plane is changed, relative to the position it would have with two components 300 of the same size. The term surface area is understood to mean the dimension orthogonal to the stacking axis of the films 101, 102 and 103. To compensate for this effect, the component 300 of smallest surface area can be stiffened by adding a compensation layer 500 consisting of a portion covering only this component 300 of smallest surface area (FIG. 7). Alternatively, the compensation layer 500 consists of several portions each covering one among several components of smaller surface area. At least one of the components is then not covered with any portion of the compensation layer 500. In the example illustrated in FIG. 7, the component of smallest surface area is directly covered with a portion of the compensation layer, on the side opposite to the first film 101. According to a variant not shown, a discrete portion of the compensation layer extends opposite the component of smallest surface area, under the first film, on the third film if it exists, or on the second film in the absence of a third film. This embodiment may or may not be combined with each of the embodiments and alternative arrangements of a compensation layer as described above.

Figure 8:
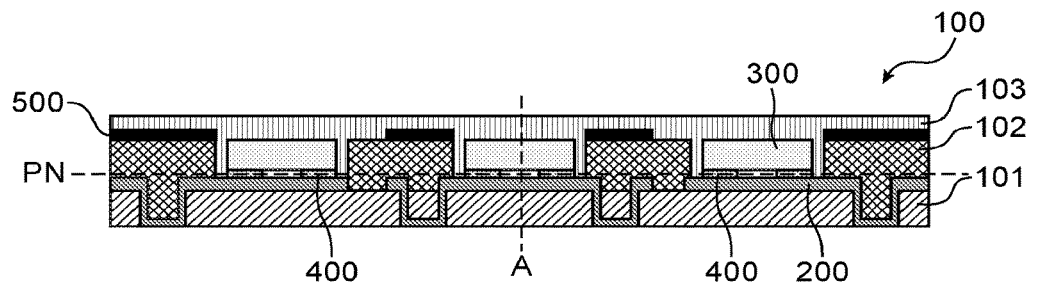
FIG. 8 is a schematic sectional and side representation of a flexible electronic structure according to an eighth embodiment of the invention.

FIG. 8 illustrates another solution for compensating for this effect, which consists in restoring to the structure 100 a plane of symmetry A passing through the component with a largest surface area. In the case where the structure 100 includes only two components 300, a third component identical to the component of smallest surface area is then added, the third component being disposed symmetrically to the component of smallest surface area relative to the plane A. In this case, the number and the position of the vias 201 will also be corrected so as to make the structure 100 as symmetrical as possible. In particular, the central component can be electrically connected to twice as many vias as the other components, for simple reasons of symmetry. Likewise, the central component is positioned here centrally above a corresponding electrical track, which is stiffened by a portion of the compensation layer open in the center.

Figure 11A:
Figure 11B:
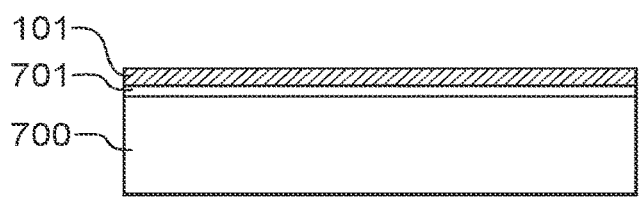
Figure 11C:
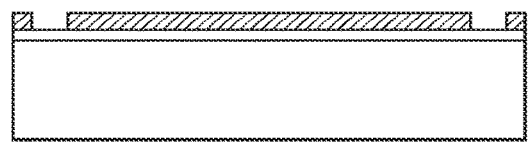
Figure 11D:
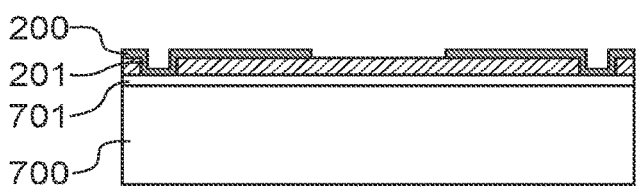
Figure 11E:
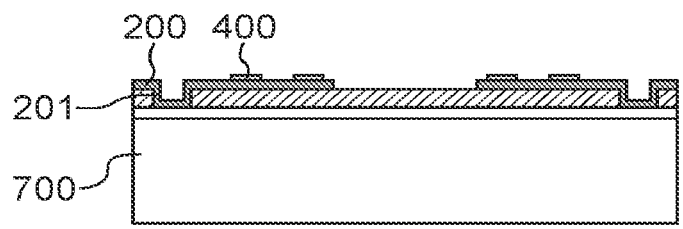
Figure 11F:
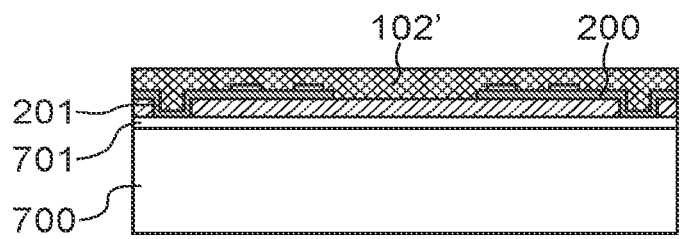
Figure 11G:
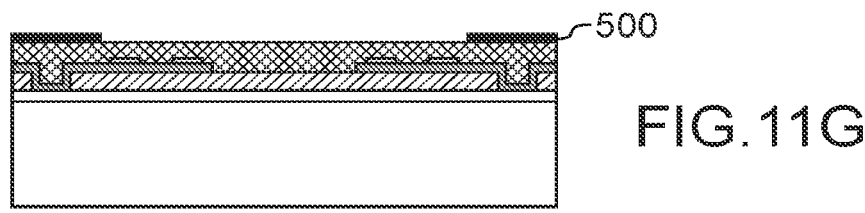
Figure 11H:
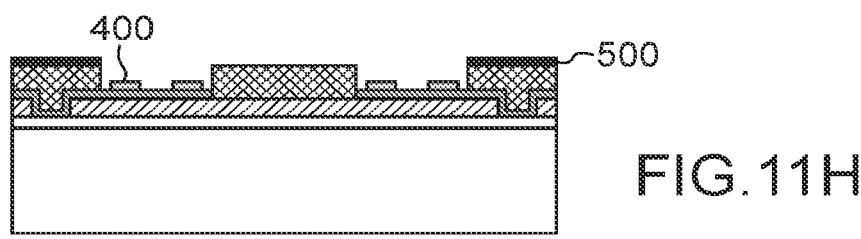

Production Method:

The method for producing such a structure 100 will now be described. The method includes the following successive steps:
  a) providing a substrate 700 (FIG. 11A),
  b) forming the first film 101 made of a first polymer or of glass (FIG. 11B),
  c) forming the at least one electrically conductive track 200 on the first film 101 (FIG. 11D),
  d) forming the second film 102 wherein is encapsulated the at least one electronic component 300, electrically connected with one of the electrically conductive tracks 200, by the respective interconnection element 400 (FIGS. 11F to 11J),
  e) optionally, forming the third film 103 (FIG. 11K),
  f) separating the substrate 700 from the flexible electronic structure 100 (FIG. 11L).

The substrate 700 is a stiff and temporary support. It is used as the basis for producing the structure 100 and will be removed when the structure is completed. It is not part of the final flexible structure 100. The support 700 is advantageously flat. The support 700 is, for example, made of silicon or of glass. The support does not need to be monocrystalline and can therefore be made of polycrystalline silicon, the cost of which is much lower.

Figure 11I:
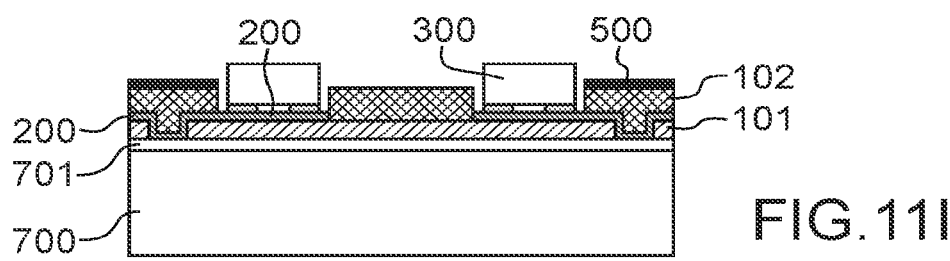
Figure 11J:
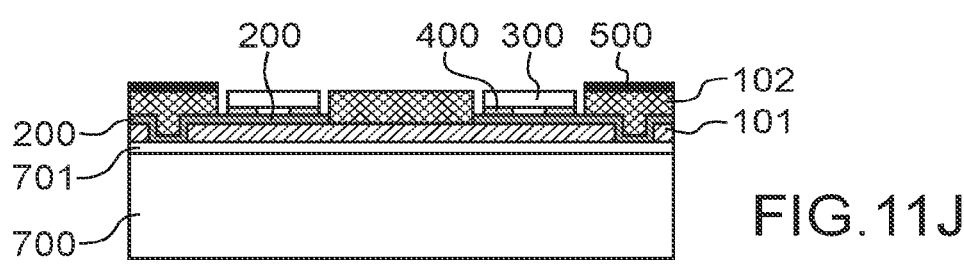
Figure 11K:
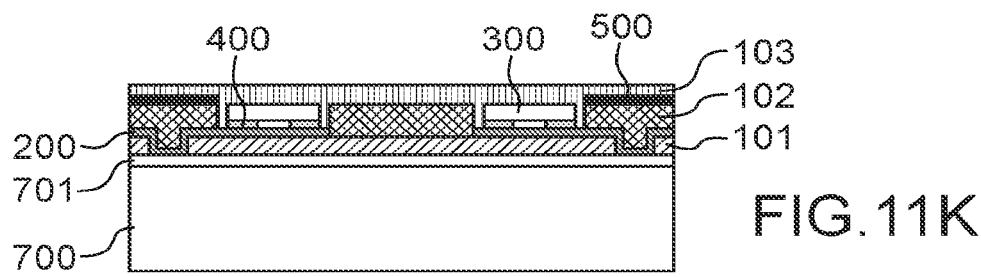
Figure 11L:
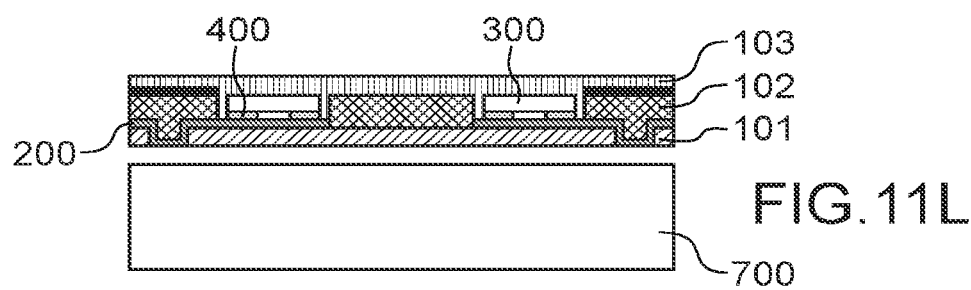
Figure 11M:
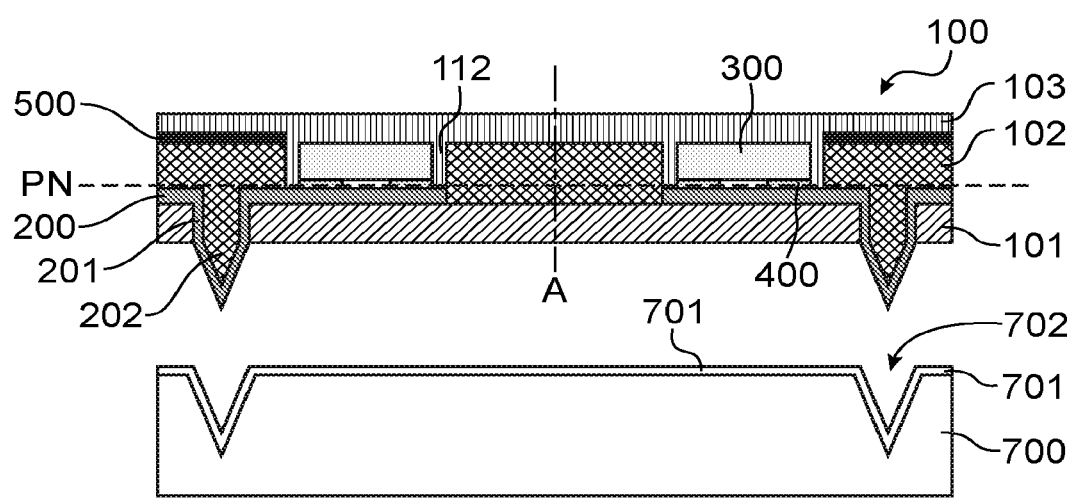

According to a variant illustrated in FIG. 11M, the substrate may contain one or more cavities 702, or recesses, thus making an indentation for the at least one metal tip 202 protruding from the first film 101. The recesses 702, which are advantageously pyramidal can be made for example by chemical etching in monocrystalline silicon.

The substrate 700 preferably comprises a sacrificial layer 701 (also called a stopper layer) which can be etched to free the structure 100 from the substrate 700, or be used as a stopper layer, in the case of mechanical thinning of the substrate 700 (step F). The sacrificial layer 701 can be made of a material that is easy to be chemically etched. When the films 101 and 103 are made of polymer, it is preferably a metal such as titanium which is etched very quickly with hydrofluoric acid.

The sacrificial layer 701 can also be a resin or an adhesive film, or a photosensitive polymer, or a stack of layers whose adhesion can be broken mechanically or thermally.

The sacrificial layer 701 can be deposited by spin-coating, by physical vapor deposition or by rolling.

According to a variant not shown, before step b), a compensation layer 500 can be formed on the substrate 700, or on the sacrificial layer if the substrate 700 comprises one, so as to be directly in contact with the first film 101. The compensation layer 500 may consist of discrete portions each extending opposite one of the electronic components, under the associated electrically conductive track, and/or opposite the one electrically conductive track. The compensation layer 500 can be deposited and etched by microelectronic methods known to the person skilled in the art.

In step b), the first film 101 is formed. The first film 101 can be deposited in the liquid state by spin-coating on the substrate 700 then thermally hardened, for example by evaporation. It can also be deposited by rolling a dry film. One or more vias 201 can be made in the first film 101 (FIG. 11C). The vias 201 can be etched by microelectronic methods known to the person skilled in the art: plasma etching, laser etching, ion etching, chemical etching. The width of the vias 201 can range from 10 to 500 µm, preferably 80 µm to 120 µm.

The electrically conductive track 200 and the interconnection element 400 are then produced (step c). The latter allows to interconnect the components by brazing, bonding, or mechanical compression during step d). When the first film 101 includes vias 201, respectively vias and protruding tips, they will be metallized during this step. The electrical tracks 200 are deposited and etched by microelectronic methods known to the person skilled in the art.

In step d), the second film 102, wherein the electronic component 300 is encapsulated, is formed. The second film 102 is, preferably, deposited in the liquid state. During the deposition, it fills the vias 201 of the underlying layer 101 (FIG. 11*f*).

In a first variant, step d) can be carried out by:
forming a solid film 102' made of the material of the second film 102 (FIG. 11F),
etching the solid film 102', so as to form at least one cavity and to make accessible the at least one electrically conductive track 200 (FIG. 11H),
transferring a respective electronic component 300 into each cavity and connecting each electronic component 300 with at least one of the electrically conductive tracks 200, each connection being made by means of a respective connection element 400 (FIG. 11I).

The cavities in the second film 102 can be etched by microelectronic methods known to the person skilled in the art: plasma etching, laser etching, ion etching, chemical etching.

After step d), and prior to the etching step, a compensation layer 500 can be formed on the second film 102 (FIG. 11G).

According to another variant, step d) can be carried out by:
transferring and connecting each electronic component 300 each on one of the electrically conductive tracks 200,
forming the second film 102 on the at least one electronic component 300 and on the first film 101.

In this variation, when the second film 102 is thick enough to completely encapsulate the components 300, both sideways and on top, there will be no need to deposit a third film 103.

The electronic components 300 are transferred, the active face down (in "flip chip"), that is to say the face including the interconnection pads facing the film 101. The transfer will be carried out by microelectronic methods known to the person skilled in the art. The second film 102 surrounds the components 300 while being able to leave a trench 112 around them. The trench 112 is then a trench called sealing trench. It will be filled with the material of the upper layer during its formation (step e).

The electrical and mechanical interconnection of the components on the electrical tracks can be made using fusible balls (for example made of SnAg, SnPb or SnAgCu etc.) or else using a conductive adhesive. It can also be made by a gold bump better known under the name of "stud bump" or "accu bump". The interconnection element 400 is formed in this step.

It may be considered to achieve a specific finish (for example in a Ti\Ni\Au multi-layer known as UBM ("Under Bump Metallization")) on the electrical tracks and/or under the pads of the electronic components, to boost bonding.

A non-conductive adhesive can be added under the components 300 so as to reinforce the mechanical cohesion.

Alternatively, the components 300 could be connected to their electrical track 200 by a mechanical assembly without fusion of the micro-insert or micro-tube type known to the person skilled in the art. This involves, for example, growing metal micro-pillars or micro-tubes, having a diameter and/or a height of a few µm to a few tens of µm, on the electrical pads of the components 300. When transferring the component 300, a sufficient pressure is exerted so that these protuberances are mechanically inserted into the host metal layer.

A thermo-compression step can be carried out to promote electrical interconnection.

In a particular embodiment, the components 300 can be thinned (FIG. 11J). The thinning of the components 300 is carried out after transferring the components 300 and before depositing the film which will cover them (film 102 or film 103 depending on the embodiment). It is produced by any microelectronic method known to the person skilled in the art, for example by grinding and/or polishing, or else by mechanical-chemical planarization (or CMP for "Chemical mechanical polishing/planarization"). The components 300 conventionally used in the microelectronics industry have thicknesses ranging from 200 µm to 700 µm. These components can be thinned to a few microns in thickness, preferably from 5 µm to 350 µm, and even more preferably from 20 µm to 70 µm.

The third film 103 is then deposited on the second film 102 and on the components 300 so as to cover them (step e, FIG. 11K). The third bendable film 103 is, preferably, deposited in the liquid state. During the deposition, it fills the sealing trenches 112 of the underlying layer.

The various films 101, 102, 103, when they are made of polymer, are advantageously formed at a temperature compatible with a rapid and controlled evaporation of the solvent containing the polymer.

According to a variant of the method not shown, after step e), a compensation layer 500 can be formed on the third film 103.

Alternatively, a thick layer of glass (about 100 µm thick) is deposited on the second film 102, which is locally etched over only a part of its thickness. Thus, a glass layer including extra thicknesses which form the discrete portions of the compensation layer 500, is produced. In other words, the glass layer after etching forms a third glass film 103 and a compensation layer 500 which are superimposed.

The structure 100 is then separated from the substrate 700 (step f, FIG. 11L).

Figure 12A:
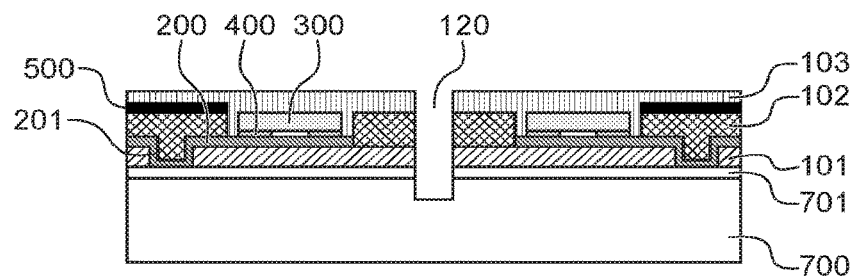
Figure 12B:
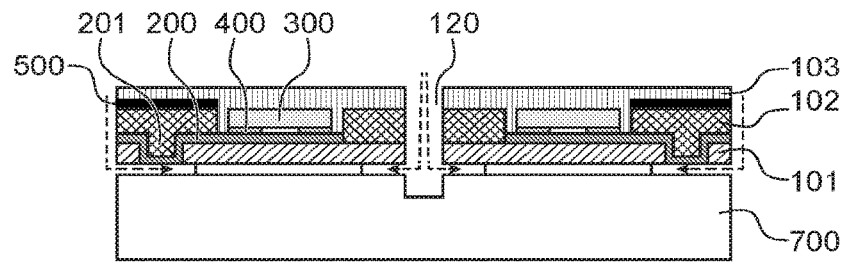

The removal of the substrate 700 will advantageously be achieved by virtue of the sacrificial layer 701. The sacrificial layer 701 can be etched to separate the substrate 700 from the flexible electronic structure 100. It can be etched chemically, for example with hydrofluoric acid. It can be attacked laterally. As shown in FIGS. 12A and 12B, before step f), one or more holes 120 passing through the structure 100, can be made so as to make the sacrificial layer 701 accessible in different locations, and not only at the edges of the substrate 700, to facilitate the etching step.

According to one variant, the sacrificial layer 701 can be removed mechanically, for example, by grinding and/or polishing. The sacrificial layer 701 can advantageously be used as a stopper layer.

Figure 13A:
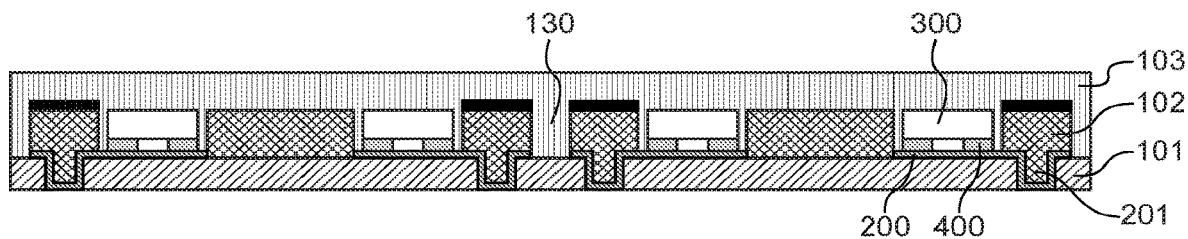
Figure 13B:
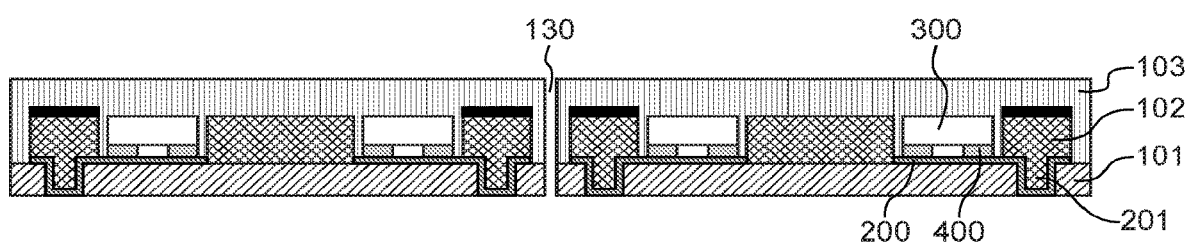

According to another embodiment, shown in FIGS. 13A and 13B, when the structure 100 comprises several components disposed in the same layer, the latter can be cut into several parts, before or after the removal of the substrate 700. Advantageously, the cutting zone 130, once cut, during the removal of the substrate 700, can be used as an infiltration zone (through-hole 120) for the etching solution, to facilitate the etching of the sacrificial layer 701.

Advantageously, the second film 102 is etched at the cutting zone 130, so as to locally form a cavity which is filled by the third film 103 during its formation. This can be of interest when it is desired to completely encapsulate the electronic components 300 in a material having specific properties, such as, for example, a biocompatibility.

The invention claimed is:

1. A flexible electronic structure comprising:
   a first film, made of a first polymer or of glass,
   a second film, made of a second polymer, wherein at least one electronic component is disposed, the second film covering the first film,
   at least one electrically conductive track, disposed between the first film and the second film, and each electrically connected to one of the at least one electronic component, by a respective interconnection element, and
   each interconnection element being disposed near a neutral plane of the structure, at a position through which a plane passes whose distance from the neutral plane is less than or equal to 20% of a total thickness of the structure,
   wherein the structure further comprises at least one discontinuous compensation layer, formed of one or more discrete portions which each extend opposite one of the at least one electrically conductive track, respectively opposite one of the at least one electronic component,
   wherein the neutral plane is located in the structure at a surface where compressive and tensile stresses compensate each other when the structure is subject to a bending process, and
   wherein a respective metal via, electrically connected to one of the at least one electrically conductive track, extends in the first film so as to connect one of the at least one electronic component through the first film, the metal via being filled with the second polymer.

2. The structure according to claim 1, further comprising a third film made of a third polymer or of glass, covering the second film.

3. The structure according to claim 2, wherein the third film and the compensation layer are made of glass, and formed together integrally.

4. The structure according to claim 2, wherein the compensation layer is disposed between the second film and the third film, consisting of portion(s) each located opposite one of the at least one electrically conductive track.

5. The structure according to claim 2, wherein the compensation layer covers the third film, and consists of portion(s) each located opposite one of the at least one electrically conductive track.

6. The structure according to claim 2, comprising at least one sealing trench, each surrounding one of the at least one electronic component, the polymer of the third film filling the sealing trench.

7. The structure according to claim 2, wherein the first polymer and the third polymer are identical.

8. The structure according to claim 2, wherein at least one through-hole extends in the first film and/or in the third film each so as to make one of the at least one electronic component accessible.

9. The structure according to claim 1, wherein the second film comprises several electronic components of different surface areas, and wherein the compensation layer covers the electronic component of smallest surface area so as to stiffen it.

10. The structure according to claim 1, wherein the compensation layer consists of portion(s) each located opposite one of the at least one electrically conductive track, the first film being disposed between the electrically conductive track and the compensation layer.

11. The structure according to claim 1, comprising two compensation layers which are separate from each other.

12. The structure according to claim 1, wherein at least one compensation layer is made of the same material as at least one electrically conductive track.

13. The structure according to claim 1, further comprising at least one metal tip, electrically connected to one of the at least one electrically conductive track by means of a corresponding via, and protruding from the first film on a side opposite to the electrically conductive track, the tip being filled with the second polymer.

14. A method for producing the flexible electronic structure according to claim 1, said method comprising the following successive steps:
   a) providing a substrate,
   b) forming the first film made of a first polymer or of glass, on the substrate,
   c) forming at least one electrically conductive track on the first film,
   d) forming the second film made of a second polymer, wherein at least one electronic component is disposed, each electronic component being electrically connected with one of the at least one electrically conductive track by a respective interconnection element, and
   e) separating the substrate from the flexible electronic structure,
   the method further comprising at least one step of forming at least one compensation layer.

15. The method according to claim 14, wherein step d) comprises the following sub-steps:
   forming a solid film made of the material of the second film,
   etching the solid film, so as to form at least one cavity, each cavity making one of the at least one electrically conductive track accessible, and
   transferring a respective electronic component into the cavities and connecting each electronic component with the at least one of the at least one electrically conductive track, each connection being made by means of a respective interconnection element.

16. The method according to claim 14, wherein step d) comprises the following sub-steps:
   transferring and connecting at least one electronic component, each with the at least one of the at least one electrically conductive track, each connection being made by means of a respective interconnection element, and
   forming the second film on the at least one electronic component and on the first film.

17. The method according to claim 14, wherein, between step a) and step b), a sacrificial layer is deposited on the support and in that during step e), the sacrificial layer is etched to separate the support from the flexible electronic structure.

18. The method according to claim 14, configured to produce a flexible electronic structure further including a third film made of a third polymer or of glass, covering the second film, wherein:
   before step b), one of the at least one compensation layer is formed on the substrate, and/or
   after step d), one of the at least one compensation layer is formed on the second film, and/or after step d), one of the at least one compensation layer is formed on the third film.

19. The method according to claim 14, wherein the first polymer is a polyimide, a polysiloxane, a parylene or a thermoplastic polymer.

20. The method according to claim 14, wherein the substrate includes at least one recess in the shape of a tip, forming an indentation to form at least one metal tip protruding from the first film, on a side opposite to the at least one electrically conductive track.

21. The structure according to claim 1, wherein the neutral plane is located between the at least one electrically conductive track and the at least one electronic component.

* * * * *